United States Patent
Gardlik et al.

(10) Patent No.: US 8,592,631 B2
(45) Date of Patent: Nov. 26, 2013

(54) PROCESS FOR THE PREPARATION OF 2-METHOXYMETHY1-1,4-BENZENEDIAMINE, ITS DERIVATIVES THEREOF AND THE SALTS THEREOF

(75) Inventors: John Michael Gardlik, Cincinnati, OH (US); Garry Steven Garrett, Fairfield, OH (US); Bryan Patrick Murphy, Loveland, OH (US); John Michael Janusz, West Chester, OH (US); John August Wos, Maineville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 22 days.

(21) Appl. No.: 13/016,272

(22) Filed: Jan. 28, 2011

(65) Prior Publication Data

US 2012/0142969 A1   Jun. 7, 2012

Related U.S. Application Data

(60) Provisional application No. 61/419,516, filed on Dec. 3, 2010.

(51) Int. Cl.
  *C07C 209/00* (2006.01)

(52) U.S. Cl.
  USPC ............ 564/398; 564/395; 564/396; 564/397

(58) Field of Classification Search
  None
  See application file for complete search history.

(56) References Cited

U.S. PATENT DOCUMENTS

| | | | |
|---|---|---|---|
| 2,273,564 | A | 2/1942 | Dickey |
| 2,507,112 | A | 5/1950 | Lippencott |
| 6,648,923 | B1 | 11/2003 | Goettel |
| 7,445,645 | B2 | 11/2008 | Sabelle |

OTHER PUBLICATIONS

Faming, Zhuanili, Shenqing, Gongkai, Shuomingshu; 101148422; Mar. 26, 2008; SciFinder.

(Continued)

*Primary Examiner* — Clinton Brooks
(74) *Attorney, Agent, or Firm* — James T. Fondriest

(57) ABSTRACT

A process for synthesizing 2-methoxymethyl-1,4-benzenediamine, its derivatives of formula (IV) and the salts thereof, which comprises a reductive amination step. The preferred final product is 2-methoxymethyl-1,4-benzenediamine of formula (IV-a).

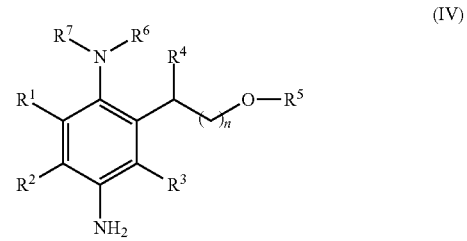

(IV)

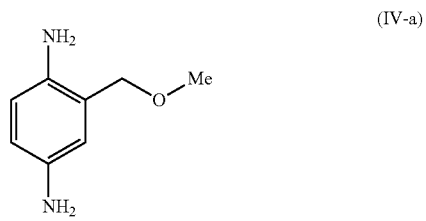

(IV-a)

These compounds may be used as primary intermediates in compositions for dyeing keratin fibers.

19 Claims, 4 Drawing Sheets

(56) References Cited

OTHER PUBLICATIONS

Ghatge; Indian (1986), IN 158329 A1; Oct. 18, 1986; SciFinder.
Anderson; The Tautomerism of Quinoneoxime; vol. 56; Mar. 1934.
Poissonnet; Preparation and; J Org. Chem 1996; 61; 2273-2282.
Dorretijn; The Reactivity of o-Hydroxybenzyl Alcohol and Derivatives in Solution at Elevated Temperatures; J. Org. Chem. 1999, 64, 3012-3018.
Silk; The Snythesis of 3-Chloro-4-nitro- and 4-Amino-3-chlorobenzyl Alcohols; 7 pgs, 1987.
Sun; Chemoselective Summary of Synthesis; Cheminform, 2008, 1 page.
Sun; Chemoselective Etherification of; Synthesis 2008, 3487-3491.

PROCESS FOR THE PREPARATION OF 2-METHOXYMETHY1-1,4-BENZENEDIAMINE, ITS DERIVATIVES THEREOF AND THE SALTS THEREOF

CROSS REFERENCE TO RELATED APPLICATION

This application claims the benefit of U.S. Provisional Application No. 61/419,516, filed Dec. 3, 2010.

FIELD OF THE INVENTION

A new process has now been developed to synthesize 2-methoxymethyl-1,4-benzenediamine (IV-a), its derivatives of formula (IV), and the salts thereof, which comprises c) a reductive amination step. These compounds may be used primary intermediates in compositions for dyeing keratin fibers.

BACKGROUND OF THE INVENTION

U.S. Pat. No. 2,273,564 discloses a process to synthesize substituted 1,4-diaminobenzene compounds with a substituent on the 2 position. U.S. Pat. No. 6,648,923 B1 discloses a process to synthesize 2-methoxymethyl-1,4-benzenediamine and the salts thereof.

The previous syntheses described above to reach 2-methoxymethyl-1,4-benzenediamine (IV-a), its derivatives, and the salts thereof are not completely satisfactory.

Therefore, there is a need for a simple, industrially applicable, efficient, not expensive and high yield process to synthesize of 2-methoxymethyl-1,4-benzenediamine (IV-a), its derivatives of formula (IV), and the salts thereof.

The key step of the process of this invention is a reductive amination involving preparation of the quinone monoxime (e.g. 2-methoxymethylnitrosophenol) as a key intermediate.

SUMMARY OF THE INVENTION

A new process has been developed to synthesize 2-methoxymethyl-1,4-benzenediamine (IV-a), its derivatives of formula (IV), and the salts thereof, which permits a production of said compounds in a novel, high yield, cost effective and simple way.

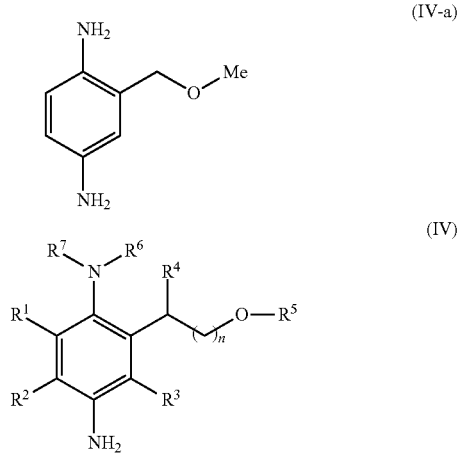

Said process comprises the step of performing a reductive amination of compounds of formula (III) in the presence of an amine, a reducing agent, and optionally reductive amination catalyst and/or more solvents to prepare compounds of formula (IV):

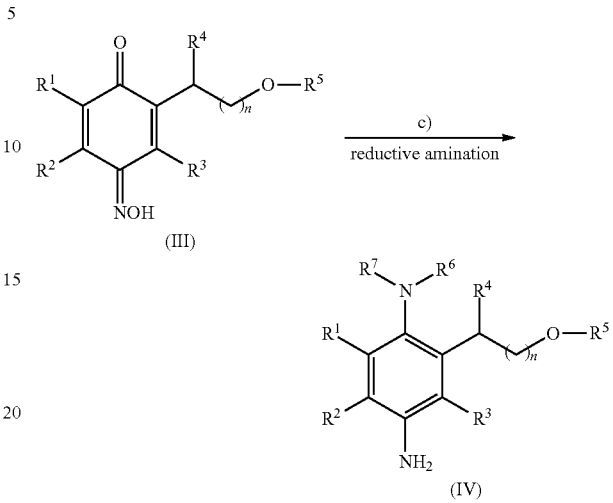

wherein $R^1$, $R^2$, $R^3$ are substituents independently selected from the group consisting of (a) C-linked substituents selected from the group consisting of:
  (i) mono- or poly-substituted or unsubstituted, straight or branched, aliphatic, heteroaliphatic, in particular alkyl, or heteroalkyl, mono- or poly-unsaturated aliphatic, in particular alkyl, or hetero unsaturated alkyl systems,
  (ii) mono- or poly-substituted or unsubstituted, mono- or poly-unsaturated aryl systems, and
  (iii) mono- or poly-substituted or unsubstituted, mono- or poly-unsaturated heteroaryl systems, and
  wherein said systems of (i), (ii) and (iii) comprise from about 1 to 10 carbon atoms and from about 0 to 5 heteroatoms selected from the group consisting of O, F, N, P and Si;
(b) S-linked substituents selected from the group consisting of $SA^1$, $SO_2A^1$, $SO_3A^1$, $SSA^1$, $SOA^1$, $SO_2NA^1A^2$, $SNA^1A^2$, and $SONA^1A^2$;
(c) O-linked substituents selected from the group consisting of $OA^1$, $ONA^1A^2$,
(d) N-linked substituents selected from the group consisting of $NA^1A^2$; $(NA^1A^2A^3)^+$, $NA^1SA^2$, $NO_2$; $NA^1A^2$;
(e) substituents selected from the group consisting of $COOA^1$, $CONA^1$, $CONA^1COA^2$, $C(=NA^1)NA^1A^2$, CN, and X;
(f) fluoroalkyl substituents selected from the group consisting of mono-, poly-, and per-fluoro alkyl systems comprising from 1 to 12 carbon atoms and from 0 to 4 heteroatoms; and
(g) hydrogen;
and mixtures thereof;

wherein $A^1$, $A^2$, and $A^3$ are substituents independently selected from the group consisting of H; substituted or unsubstituted, straight or branched, alkyl, mono- or poly-unsaturated alkyl, heteroalkyl, aliphatic, heteroaliphatic, or heteroolefinic systems; substituted or unsubstituted, mono- or poly-cyclic aliphatic, aryl, or heterocyclic systems; and substituted or unsubstituted, mono-, poly-, or per-fluoro alkyl systems, or $A^1$ and $A^2$ together with nitrogen atoms to which they are bound form a ring; wherein said systems comprise from 1 to 10 carbon atoms and from 0 to 5 heteroatoms selected from the group consisting of O, S, N, P, and Si; and wherein X is a halogen selected from the group consisting of F, Cl, Br, I, and mixtures thereof;

wherein R⁴ is a substituent independently selected from the group consisting of hydrogen, a hydroxyalkyl, a mono- or poly-substituted or unsubstituted, straight or branched, aliphatic, heteroaliphatic, in particular alkyl, or heteroalkyl; mono- or poly-substituted or unsubstituted, straight or branched unsaturated aliphatic, in particular hydroxyalkyl, unsaturated alkyl, or hetero unsaturated alkyl systems and mixtures thereof;

wherein R⁵ is a substituent independently selected from the group consisting of hydrogen, a mono- or poly-substituted or unsubstituted, straight or branched, aliphatic, heteroaliphatic, in particular alkyl, or heteroalkyl; mono- or poly-substituted or unsubstituted, straight or branched unsaturated aliphatic, in particular unsaturated alkyl, or hetero unsaturated alkyl systems and mixtures thereof;

wherein R⁶ and R⁷ is selected from the group consisting of hydrogen, hydroxyl, alkyl, hetereo alkyl, mono-, or poly-hydroxyalkyl, mono- or poly-hydroxy hetero alkyl;

wherein when R⁴ is —CH₂OH and R⁵ is —H, each hydroxyl function of the corresponding diol is optionally protected with a protecting group;

wherein n is equal to 0, 1, 2, or 3, preferably 0 or 1, more preferably 0.

Said process further comprising the step of inserting a nitroso function into compounds of formula (II) in the presence of a nitrosation agent and one or more solvents to prepare compounds of formula (III)

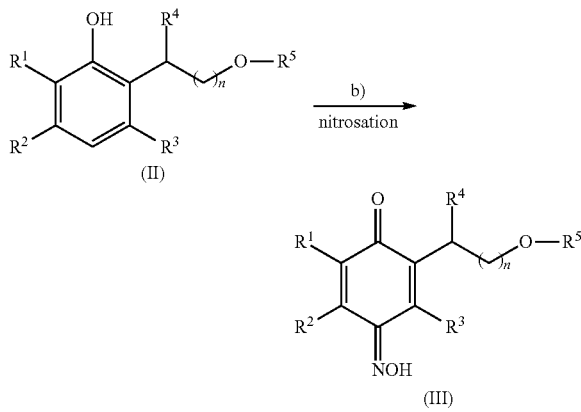

wherein R¹, R², R³, R⁴, R⁵ are substituents and n is an indicia as defined above; and wherein the phenolic hydroxyl substituent of compound (II) optionally comprises a protecting group.

Said process further comprising the step of alkylating compounds of formula (I) in the presence of an alkylating agent, neat or in the presence of one or more solvents to prepare compounds of formula (II),

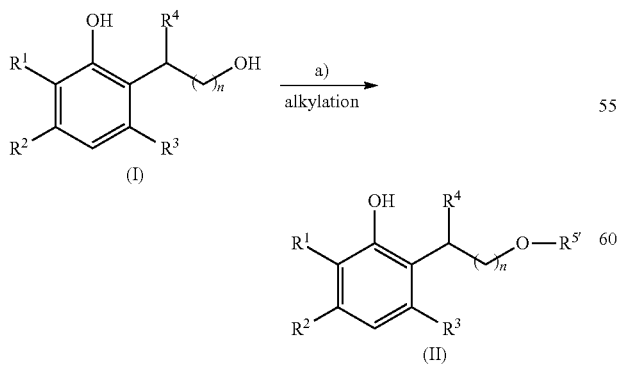

wherein R¹, R², R³, R⁴ are substituents and n is an indicia as defined previously; and wherein R⁵'is a substituent independently selected from the group consisting of a mono- or poly-substituted or unsubstituted, straight or branched, aliphatic, heteroaliphatic, in particular alkyl, or heteroalkyl; mono- or poly-substituted or unsubstituted, straight or branched unsaturated aliphatic, in particular unsaturated alkyl, or hetero unsaturated alkyl systems and mixtures thereof; and wherein the phenolic hydroxyl substituent of compound (II) optionally comprises a protecting group.

In this specification, the term "substituted" refers to the following non limiting groups of; aliphatic, heteroaliphatic, in particular alkyl; or heteroalkyl; mono- or poly-unsaturated aliphatic, in particular alkyl; or hetero unsaturated alkyl systems; mono- or poly-unsaturated aryl systems; mono- or poly-unsaturated heteroaryl systems; and wherein said systems comprise from about 1 to 10 carbon atoms and from about 0 to 5 heteroatoms selected from the group consisting of O, F, N, P and Si and mixtures thereof.

The skilled person would judge on the necessity to use a protecting group during the process of this invention. Protecting groups are widely used in chemistry and the skilled person willing to use the process described in this invention would use his common general knowledge and books dedicated to that purpose such as "Greene's Protective Groups in Organic Synthesis" by Peter G. M. Wuts, Theodora W. Greene, Wiley-Interscience; 4 edition (Oct. 30, 2006) or "Protecting groups" by Philip J. Kocienski, Thieme, Stuttgart; Auflage: 3rd Revised edition (14. February 2005).

And consequently, if the skilled person decides to use a protecting group during the process, he would then decide to add extra deprotection step, to remove the protecting group.

DETAILED DESCRIPTION OF THE INVENTION

Figure 1:
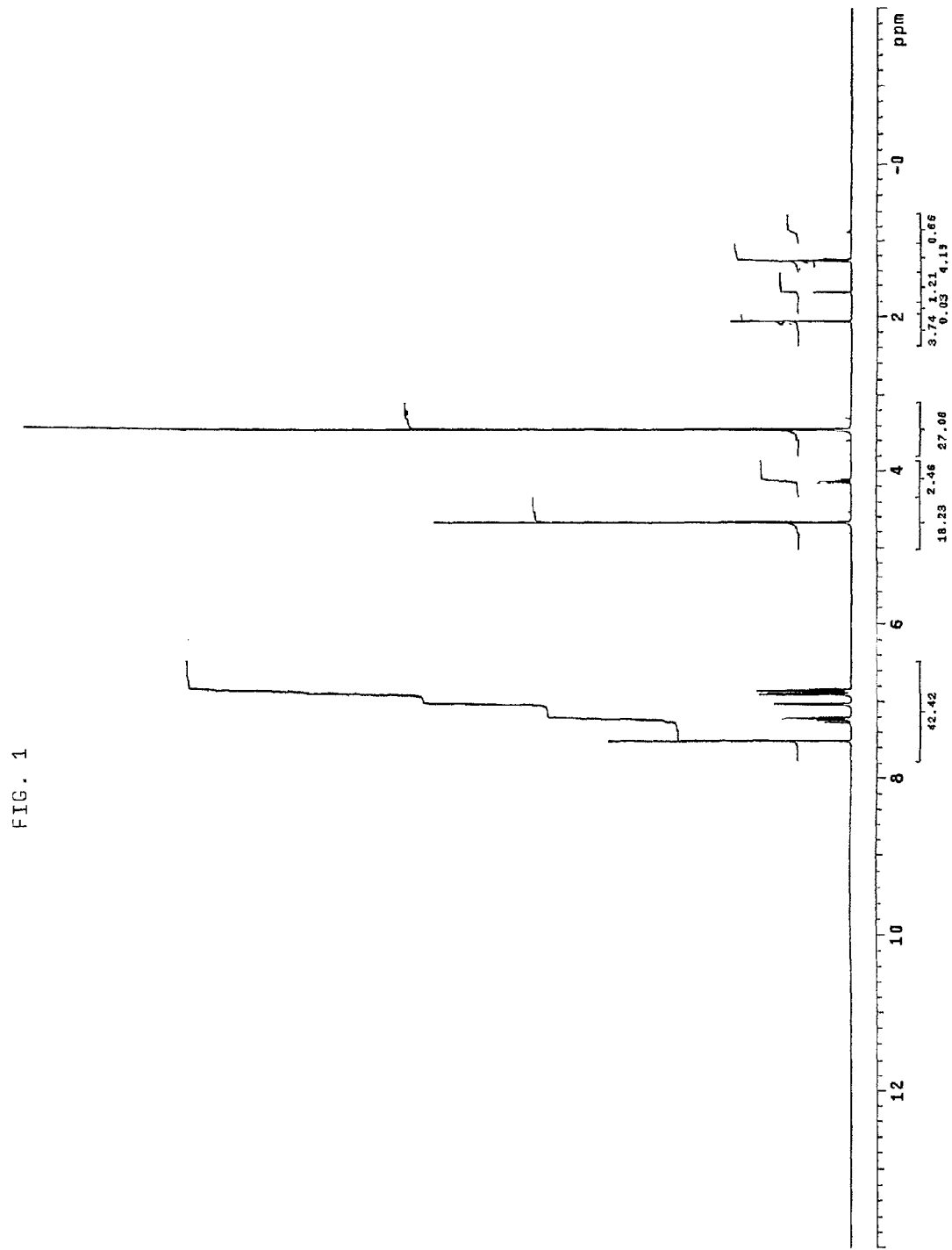
FIG. 1 ¹HNMR of compound II-a resulting from step a)
FIG. 2 ¹HNMR of compound III-a resulting from step b)
FIG. 3 ¹HNMR of compound VI-a resulting from step d)
FIG. 4 ¹HNMR of compound IV-a resulting from step e)
Figure 2:
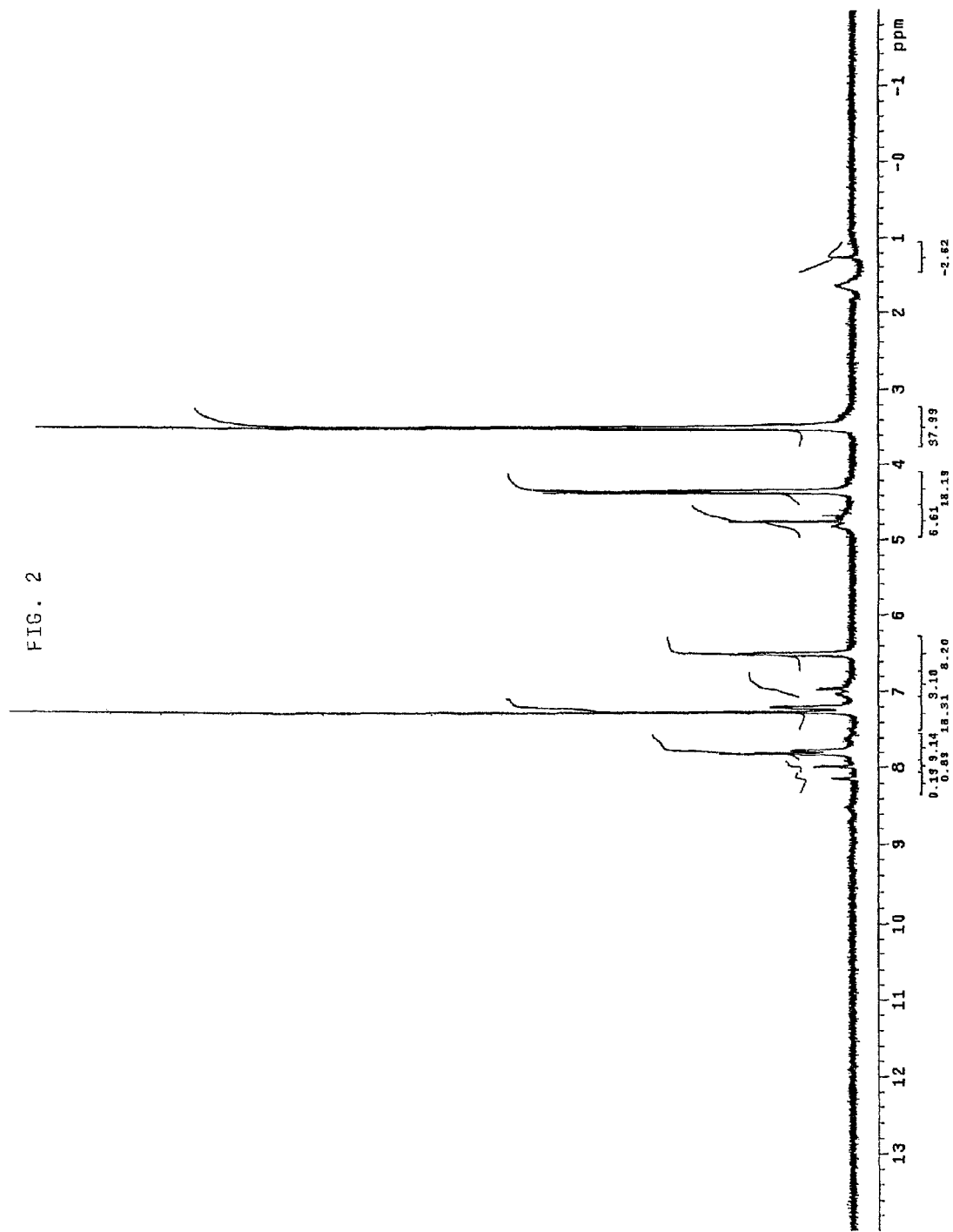
Figure 3:
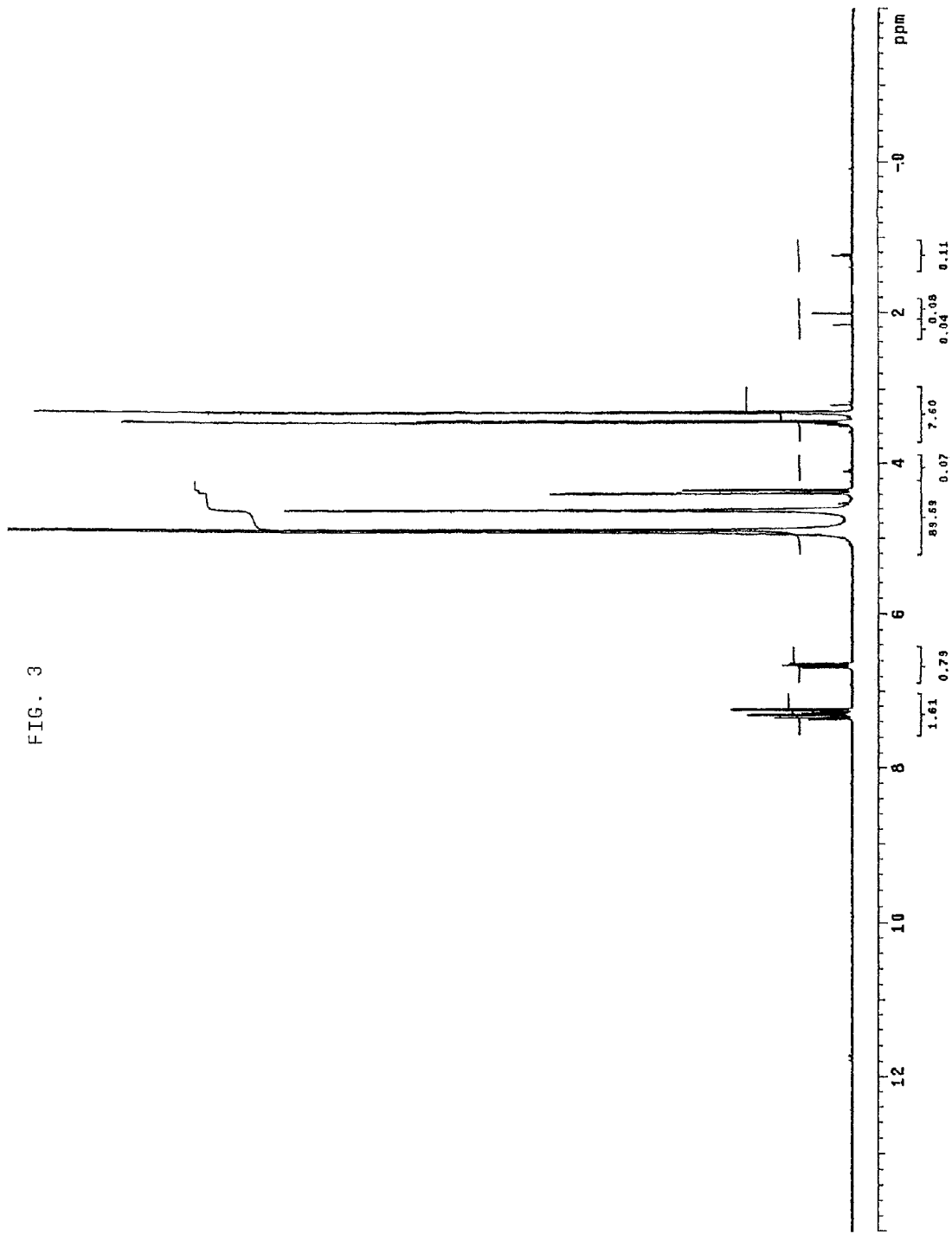
Figure 4:
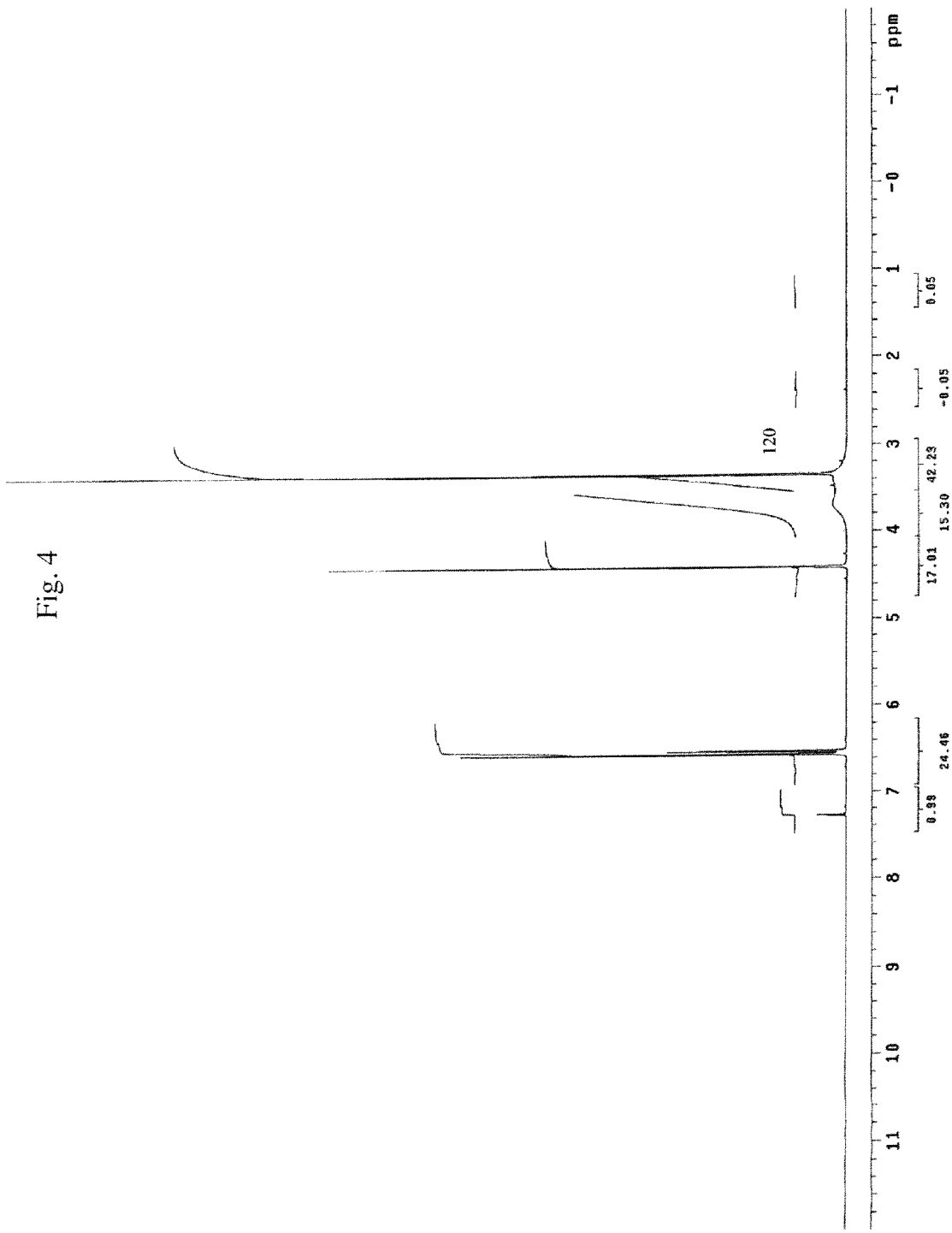

The different steps used in the present invention will now be detailed.

I. The reductive amination step c) consisting of performing a reductive amination of compound (III) with an amine, a reducing agent, and optionally a reductive amination catalyst in one or more solvents to prepare compounds of formula (IV):

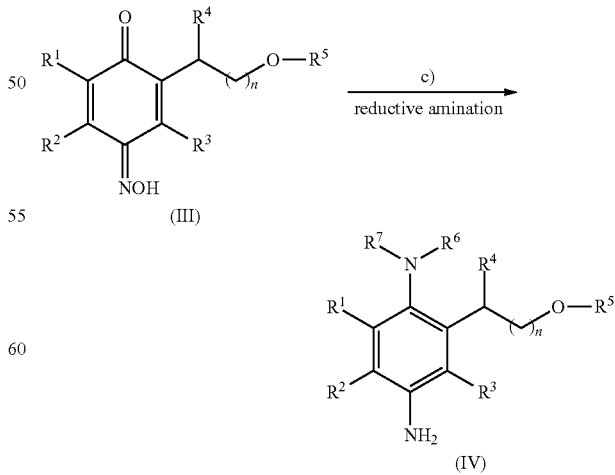

Non limiting examples of solvents for the reductive amination step c) comprise pentane, cyclopentane, hexane, cyclohexane, benzene, toluene, 1,4-dioxane, chloroform, diethyl ether, dichloromethane, tetrahydrofuran, methyl-tetrahydrofuran, dimethylformamide, acetonitrile, dimethyl sulfoxide, n-butanol, isopropanol, n-propanol, ethanol, methanol, and mixtures thereof.

Non limiting examples of amines for the reductive amination step c) comprise compounds of formula $R^6R^7NH$, in particular hydroxylamine, or ammonia or the salts of thereof.

Non limiting examples of reducing agents for the reductive amination step c) comprise hydrazine, $H_2$, $LiAlH_4$, $LiBH_4$, DIBAL-H, $NaBH_4$, $NaCNBH_3$, $B_2H_6$, sodium hydrosulfite, sodium sulfide and mixtures thereof.

Non limiting examples of reductive amination catalysts for the reductive amination step c) comprise Raney nickel, nickel, palladium, Lindlar catalyst, cobalt, copper chromite, platinium, platinum oxide, rhenium, tin(II) chlorie, titanium(III) chloride, zinc, samarium, iron and mixtures thereof.

wherein $R^1$, $R^2$, $R^3$, $R^4$, $R^5$, $R^6$ and $R^7$ are substituents and n is an indicia as defined previously in the "Summary of the invention" section, the reductive amination step c).

I.1. The Reductive Amination Step c)

The reductive amination step c) can be performed; either by direct reductive amination, i.e. wherein the steps d) and e) are performed in a one pot reaction or by indirect reductive amination, i.e. wherein the steps d) and e) are performed successively.

I.1.a Performing a condensation step d) by reacting compounds (III) with an amine, neat or in one or more solvents to prepare compounds of formula (VI):

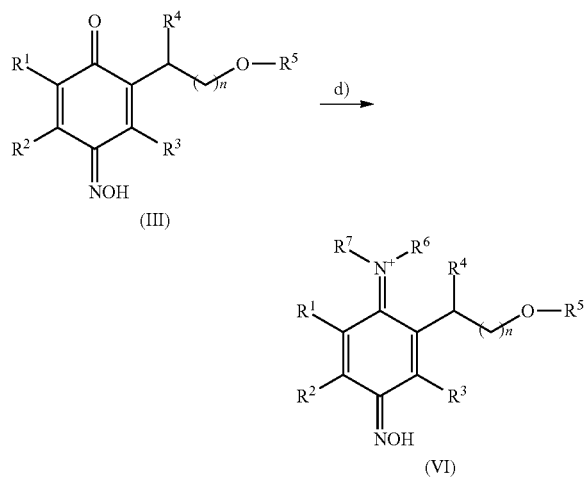

wherein $R^1$, $R^2$, $R^3$, $R^4$, $R^5$, $R^6$ and $R^7$ are substituents and n is an indicia as defined previously in the "Summary of the invention" section, the reductive amination step c).

Non limiting examples of solvents for the condensation step d) comprise pentane, cyclopentane, hexane, cyclohexane, benzene, toluene, 1,4-dioxane, chloroform, diethyl ether, dichloromethane, tetrahydrofuran, methyl-tetrahydrofuran, ethyl acetate, acetone, dimethylformamide, acetonitrile, dimethyl sulfoxide, n-butanol, isopropanol, n-propanol, ethanol, methanol and mixtures thereof.

Non limiting examples of amines for the condensation step d) comprise compounds of formula $R^6R^7NH$, in particular hydroxylamine, or ammonia or the salts of thereof.

I.1.b Performing a reductive step e) by reacting compounds (VI) in presence of a reducing agent, and optionally reductive amination catalyst, neat or in one or more solvents to prepare compounds of formula (IV):

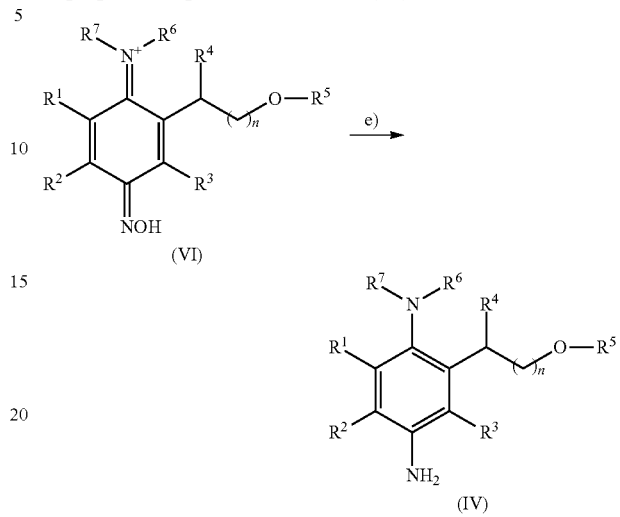

wherein $R^1$, $R^2$, $R^3$, $R^4$, $R^5$, $R^6$ and $R^7$ are substituents and n is an indicia as defined previously in the "Summary of the invention" section, the reductive amination step c).

Non limiting examples of solvents for the reductive step e) comprise pentane, cyclopentane, hexane, cyclohexane, benzene, toluene, 1,4-dioxane, diethyl ether, tetrahydrofuran, methyl-tetrahydrofuran, ethyl acetate, acetone, dimethylformamide, acetonitrile, dimethyl sulfoxide, n-butanol, isopropanol, n-propanol, ethanol, methanol and mixtures thereof.

Non limiting examples of reducing agents for the reductive step e) comprise hydrazine, $H_2$, $LiAlH_4$, $LiBH_4$, DIBAL-H, $NaBH_4$, $NaCNBH_3$, $B_2H_6$, sodium hydrosulfite, sodium sulfide and mixtures thereof.

Non limiting examples of reductive amination catalysts for the reductive step e) comprise Raney nickel, nickel, palladium, Lindlar catalyst, cobalt, copper chromite, platinium, platinum oxide, rhenium, tin(II) chloride, titanium(III) chloride, zinc, samarium, iron and mixtures thereof.

II. The nitrosation second step b) consists of inserting a nitroso function into compound (ii) with a nitrosation agent in one or more solvents to prepare compounds of formula (iii):

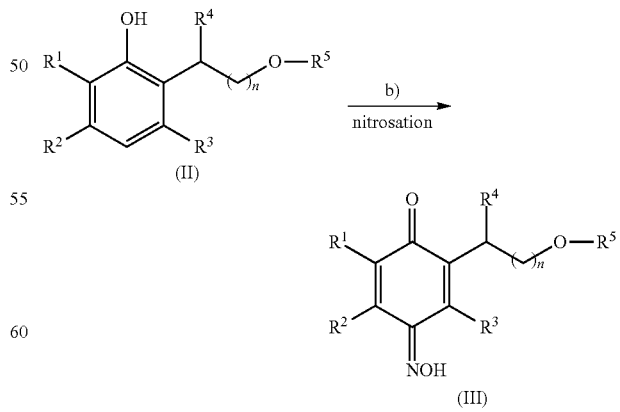

It is important to note that adduct of the nitrosation reaction lead to 4-nitrosophenol (also called p-nitrosophenol or 4-hydroxynitrobenzene), which is in an equilibrium with its tautomer; the quinoneoxime (cf. Leigh C. Anderson, R. L. Yanke, *J. Am. Chem. Soc.*, 1934, 56 (3), pp 732-735).

Hence, the formula for compounds (III) includes also its tautomer (III-t);

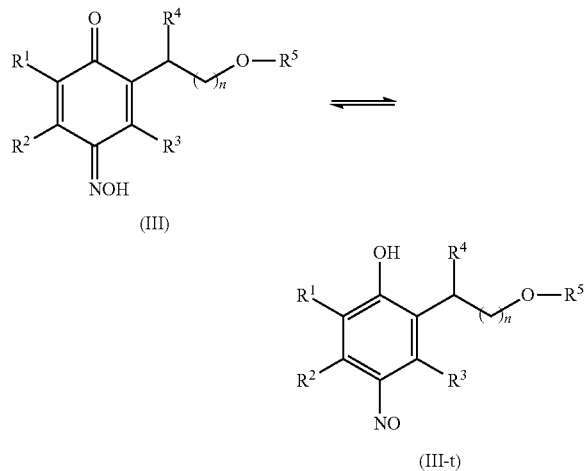

Non limiting examples of solvents for the nitrosation step b) comprise water, pentane, cyclopentane, hexane, cyclohexane, benzene, toluene, 1,4-dioxane, chloroform, diethyl ether, dichloromethane, tetrahydrofuran, methyl-tetrahydrofuran, ethyl acetate, acetone, dimethylformamide, acetonitrile, dimethyl sulfoxide, n-butanol, isopropanol, n-propanol, ethanol, methanol and mixtures thereof.

Non limiting examples of nitrosation agents for the nitrosation step b) comprise $NaNO_2$ and $H_2SO_4$; $NaNO_2$ and NaOH; isoamyl nitrite ($i-AmNO_2$) and $K_2CO_3$ and mixtures thereof.

wherein $R^1, R^2, R^3, R^4, R^5$ are substituents and n is an indicia as defined previously in the "Summary of the invention" section, the reductive amination step c).

III. The alkylating step a) consists of alkylating compound (i) with an alkylating agent neat or in one or more solvents to prepare compounds of formula (ii):

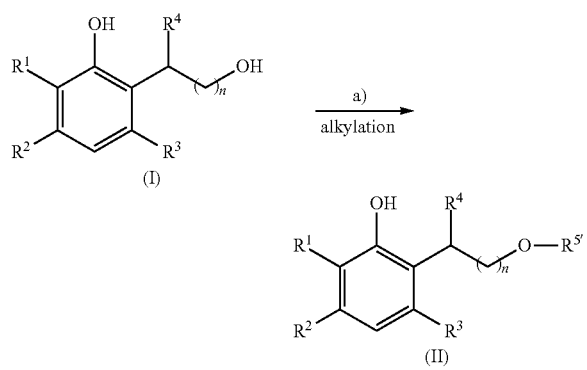

Non limiting examples of solvents for the alkylation step a) comprise pentane, cyclopentane, hexane, cyclohexane, benzene, toluene, 1,4-dioxane, chloroform, diethyl ether, dichloromethane, tetrahydrofuran, methyl-tetrahydrofuran, ethyl acetate, acetone, dimethylformamide, acetonitrile, dimethyl sulfoxide, n-butanol, isopropanol, n-propanol, ethanol, methanol and mixtures thereof.

Non limiting examples of alkylating agents for the alkylation step a) can be selected from the group consisting of: methanol, $(C_1-C_4)$—I, $(C_1-C_4)$—Cl, $(C_1-C_4)$—Br, $Me_2SO_4$ and mixtures thereof.

wherein $R^1, R^2, R^3$ are substituents independently selected from the group consisting of
(a) C-linked substituents selected from the group consisting of:
   (i) mono- or poly-substituted or unsubstituted, straight or branched, aliphatic, heteroaliphatic, in particular alkyl, or heteroalkyl, mono- or poly-unsaturated aliphatic, in particular alkyl, or hetero unsaturated alkyl systems,
   (ii) mono- or poly-substituted or unsubstituted, mono- or poly-unsaturated aryl systems, and
   (iii) mono- or poly-substituted or unsubstituted, mono- or poly-unsaturated heteroaryl systems, and
wherein said systems of (i), (ii) and (iii) comprise from about 1 to 10 carbon atoms and from about 0 to 5 heteroatoms selected from the group consisting of O, F, N, P and Si;
(b) S-linked substituents selected from the group consisting of $SA^1$, $SO_2A^1$, $SO_3A^1$, $SSA^1$, $SOA^1$, $SO_2NA^1A^2$, $SNA^1A^2$, and $SONA^1A^2$;
(c) O-linked substituents selected from the group consisting of $OA^1$, $ONA^1A^2$;
(d) N-linked substituents selected from the group consisting of $NA^1A^2$; $(NA^1A^2A^3)^+$, $NA^1SA^2$, $NO_2$; $NA^1A^2$;
(e) substituents selected from the group consisting of $COOA^1$, $CONA^1$, $CONA^1COA^2$, $C(=NA^1)NA^1A^2$, CN, and X;
(f) fluoroalkyl substituents selected from the group consisting of mono-, poly-, and per-fluoro alkyl systems comprising from 1 to 12 carbon atoms and from 0 to 4 heteroatoms; and
(g) hydrogen;
and mixtures thereof;
wherein $A^1$, $A^2$, and $A^3$ are substituents independently selected from the group consisting of H; substituted or unsubstituted, straight or branched, alkyl, mono- or poly-unsaturated alkyl, heteroalkyl, aliphatic, heteroaliphatic, or heteroolefinic systems; substituted or unsubstituted, mono- or poly-cyclic aliphatic, aryl, or heterocyclic systems; and substituted or unsubstituted, mono-, poly-, or per-fluoro alkyl systems, or $A^1$ and $A^2$ together with nitrogen atoms to which they are bound together to form a ring;
wherein said systems comprise from 1 to 10 carbon atoms and from 0 to 5 heteroatoms selected from the group consisting of O, S, N, P, and Si; and
wherein X is a halogen selected from the group consisting of F, Cl, Br, I, and mixtures thereof;
wherein $R^1$ is preferably hydrogen, alternatively a straight alkyl chain, alkoxy substitutent, alkoxyalkyl substitutent, alternatively alkoxy substituent.
wherein $R^2$ is preferably hydrogen, alternatively a straight alkyl chain, alkoxy substitutent, alkoxyalkyl substitutent, alternatively alkoxy substituent, alternatively a methoxy substituent;
wherein $R^3$ is preferably a hydrogen;
wherein $R^4$ is a substituent independently selected from the group consisting of a hydrogen hydroxyalkyl, mono- or poly-substituted or unsubstituted, straight or branched, aliphatic, heteroaliphatic, in particular alkyl, or heteroalkyl, mono- or poly-unsaturated aliphatic, in particular alkyl, or hetero unsaturated alkyl systems and mixtures thereof. $R^4$ is preferably hydrogen, alternatively a hydroxyalkyl, straight alkyl chain, alkoxy substitutent, alkoxyalkyl substitutent, alternatively alkoxy substituent, even alternatively $CH_2$—OH substituent;

wherein R⁵' is a substituent independently selected from the group consisting of mono- or poly-substituted or unsubstituted, straight or branched, aliphatic, heteroaliphatic, in particular alkyl, or heteroalkyl; mono- or poly-substituted or unsubstituted, straight or branched unsaturated aliphatic, in particular unsaturated alkyl, or hetero unsaturated alkyl systems and mixtures thereof; R⁵' is preferably a straight alkyl chain, alkoxy substitutent, alkoxyalkyl substitutent, alternatively alkoxy substituent, alternatively a CH₃ substituent;

wherein when R⁴ is CH₂OH and R⁵ is H, each hydroxyl function of the corresponding diol is optionally protected with a protecting group; and wherein n is equal to 0, 1, 2, or 3, preferably 0 or 1, more preferably 0.

Alkylating regioselectively compound (I) neat or in one or more solvents to prepare compound (II).

The alkylation step a) described above can be carried out; either by performing an A) O-activation using at least an O-activating agent and a nucleophilic alkylating agent or B) Using an alkoxide of formula (V) as a nucleophile, and an electrophilic alkylation agent, and/or base. Thus, in the present invention the term "alkylating agent" comprises nucleophilic alkylating agent and electrophilic alkylation agent.

A/ Performing an O-activation using at least an O-activating agent and a nucleophilic alkylating agent;

The alkylation could be carried out using conventional methods; i.e. using at least one O-activating agent and at least a nucleophilic alkylating agent.

Nucleophilic alkylating agents deliver the equivalent of an alkyl anion (carbanion). Examples include the use of organometallic compounds such as Grignard (organomagnesium), organolithium, organocopper, and organosodium reagents. These compounds typically can add to an electron-deficient carbon atom such as an O-activating group.

Non limiting examples of O-activating agents comprise triphenylphosphine, diethyl azodicarboxylate (DEAD), diisopropyl azodicarboxylate (DIAD), tosyl chloride, mesyl chloride and mixture thereof.

Alternatively, the OH group could be transformed to a leaving group such as an H₂O or a halide (Cl, Br, I), enabling thus the nucleophilic alkylating agents to displace the leaving group and form the desired ether derivatives of formula (II).

When using the conditions cited above and desiring to perform an alkylation on the benzylic primary alcohol, the skilled person in the art would also judge on the necessity to add or not protecting group on the acidic phenolic alcohol.

When willing to avoid the use of a protecting group, the skilled person would look for chemoselective conditions to reach the ether derivatives of formula (II). Synthesis 2008, 21, 3487-3491 describes for example a chemoselective etherification of benzyl alcohol using 2,4,6-trichloro-1,3,5-triazine and methanol or ethanol catalyzed by dimethyl sulfoxide.

B/ Using an alkoxide of formula (V) as a nucleophile, and an electrophilic alkylating agent, and/or a base.

The alkylation could also be carried out using other conventional methods; i.e. using at least one non limiting examples of base to generate an alkoxide of formula (V) and at least one electrophilic alkylating agent.

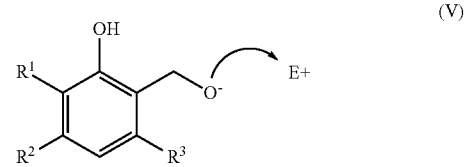

(V)

Electrophilic alkylating agents deliver "E+" the equivalent of an alkyl cation.

Non limiting examples of electrophilic alkylating agents comprise methanol, ($C_1$-$C_4$)—I, ($C_1$-$C_4$)—Br, ($C_1$-$C_4$)—Cl, $Me_2SO_4$ and mixtures thereof.

Non limiting examples of bases comprise sodium hydroxide—NaOH, potassium hydroxide—KOH, ammonium hydroxide—$NH_4OH$, calcium hydroxide—$Ca(OH)_2$, magnesium hydroxide—$Mg(OH)_2$, barium hydroxide—$Ba(OH)_2$, aluminum hydroxide—$Al(OH)_3$, ferrous hydroxide or Iron (II) hydroxide—$Fe(OH)_2$, ferric hydroxide or Iron (III) hydroxide-$Fe(OH)_3$ Zinc hydroxide—$Zn(OH)_2$, lithium hydroxide—LiOH, sodium bicarbonate and mixtures thereof.

When using the conditions cited above and desiring to perform an alkylation on the benzylic primary alcohol, the skilled person in the art would also judge on the necessity to add or not protecting group on the phenolic hydroxyl substituent.

Non limiting examples of protecting groups for the phenolic hydroxyl substituent are:

Ethers; Methyl ethers, Methoxymethyl ether MOM, Methoxyethoxymethyl ethers (MEM), Methyl Thiomethyl Ethers (MTM), Benzyloxymethyl Ethers (BOM), Tetrahydropyranyl Ether (THP), Ethoxyethyl ethers (EE), Benzyl Ethers (R-OBn), 2-Napthylmethyl Ethers (NAP), p-Methoxybenzyl Ethers (PMB), o-Nitrobenzyl ethers, p-Nitrobenzyl Ether, 9-Phenylxanthyl-(pixyl, px), Trityl Ethers, Methoxytrityl Ethers.

Silyl Ethers Trimethylsilyl ethers (TMS-OR), Triethylsilyl ethers (TES-OR), Triisopropylsilyl ethers (TIPS—OR), Phenyldimethylsilyl ethers, t-Butyldimethylsilyl Ether (TBS-OR or TBDMS-OR), t-Butyldiphenylsilyl Ether (TBDPS-OR).

Esters: Activated Acids. $RCO_2H$→"activated acid"→ carboxylic acid derivative (ester, amide, etc.) See Chem. Soc. Rev. 1983, 12, 129 or Angew. Chem. Int. Ed. Engl. 1978, 17, 569. Acetates: R—OH→$RO_2CCH_3$→"activated acetates"→chloroacetates, trifluoroacetates, pivaloate (t-butyl ester), Benzoate (Bz).

Non limiting examples of protecting groups for the diol substituent (see Synthesis, 1981, 501) Isopropylidenes (acetonides), cycloalkylidene Ketals, benzylidene Acetals, p-Methoxybenzylidenes, carbonates, di-t-Butylsilylene (DTBS), 1,3-(1,1,3,3)-tetraisopropyldisiloxanylidene (TIPDS).

When willing to avoid the use of a protecting group, the skilled person would look for chemoselective conditions to reach the ether derivatives of formula (II).

It is to be understood that the steps of alkylation, nitrosation and reductive amination, involved in the synthetic sequence leading to the desired compounds of formula (IV) are performed with the steps of b) nitrosation then c) reductive amination and a) alkylating done successively, or wherein the steps of a) alkylating, b) nitrosation and c) reductive amination steps are performed successively.

V. Application of the process above to the total synthesis 2-methoxymethyl-1,4-benzenediamine (iv-a)

The process described above can been utilized to synthesize 2-methoxymethyl-1,4-benzenediamine of formula (IV-a).

The steps are described in the following paragraphs.

V.a The step a) consists of methylating regioselectively 2-hydroxymethylphenol (i-a) in methanol to prepare 2-methoxymethyl-phenol (ii-a):

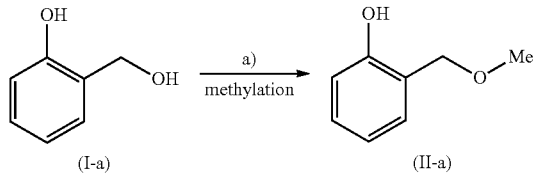

The methylation step a) is performed at a temperature from 0° C. to 200° C., preferably from 145° C. to 155° C.

The first step in the sequence to prepare 2-methoxymethyl-1,4-benzenediamine is the selective methylation of 2-hydroxymethyl-phenol (I-a) to produce 2-methoxymethyl phenol (II-a). This can be accomplished inexpensively and in extremely high yield according to the method described in The Reactivity of o-Hydroxybenzyl Alcohol and Derivatives in Solution at Elevated Temperatures published in J. Org. Chem. 1999, 64, 3012-3018. The mechanism of this highly regioselective methylation is discussed in the paper.

V.b The step b) consists of inserting regioselectively a nitroso function to 2-methoxymethyl-phenol (ii-a) in presence of a non limiting examples of source of nitroso function and one or more solvents to prepare 2-methoxymethyl[1,4]-benzoquinone 4-oxime (M-a):

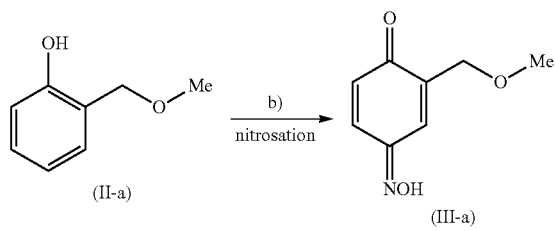

The nitrosophenol (III-a) (e.g. quinone monoxime) is then prepared from (II-a) under acid conditions as disclosed in the patent Process For The Manufacture of p-nitrosophenol U.S. Pat. No. 3,320,324, 1967 using sodium nitrite and sulfuric acid in water. Additional methods to prepare (II-a) under acidic conditions are disclosed in Tetrahedron, 1995, 51, 8447-8458. The material may also be prepared under basic conditions according to the patent Preparation of para-Quinone Dioxime U.S. Pat. No. 2,507,112, 1950 using sodium nitrite and sodium hydroxide in water. The material may also be prepared under alternative basic conditions using isoamyl nitrite in DMF with potassium carbonate according to the procedure in J. Org. Chem., 1996, 61, 2774-2779.

Non limiting examples of sources of nitroso function for the nitrosation step b) comprise $NaNO_2$ and $H_2SO_4$; $NaNO_2$ and NaOH; isoamyl nitrite (i-$AmNO_2$) and $K_2CO_3$; preferably $NaNO_2$ and $H_2SO_4$ and mixtures thereof.

Non limiting examples of solvents for the nitrosation step b) comprise pentane, cyclopentane, hexane, cyclohexane, benzene, toluene, 1,4-dioxane, chloroform, diethyl ether, dichloromethane, tetrahydrofuran, methyl-tetrahydrofuran, dimethylformamide, acetonitrile, dimethyl sulfoxide, n-butanol, isopropanol, n-propanol, ethanol, methanol and mixtures thereof, more preferably water.

The nitrosation step b) can be performed at basic pH, wherein the pH range can be from 4 to 10.

The nitrosation step b) can be performed at acidic pH, wherein the pH range can be from 1 to 4, preferably from 2 to 3, more preferably 2.4-2.5.

The nitrosation step b) can be performed at a temperature from −30° C. to 50° C., preferably below 10° C.

V.c The step d) consists of performing a condensation by reacting 2-methoxymethyl-[1,4]-benzoquinone-4-oxime (iii-a) with hydroxylamine, in presence of a base and one or more solvents to prepare 2-methoxymethyl-[1,4]-benzoquinone dioxime (vi-a):

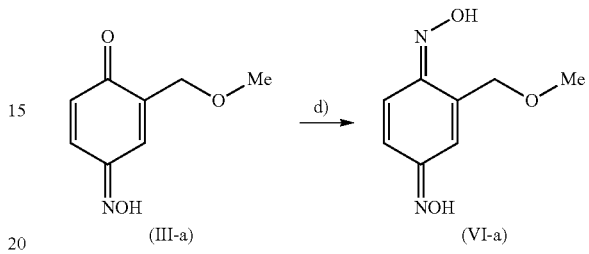

The dioxime (VI-a) can be then prepared via condensation of the nitrosophenol (III-a) with hydroxylamine hydrochloride in alcohol solvent (Ethanol) with potassium carbonate as base. This method can be adapted from methods used to prepare the dioxime directly from the para-quinone. It is found that excess hydroxylamine hydrochloride (5-10 equivalents) leads to very clean conversion. The final method was adapted from several sources such as: Faming Zhuanli Shenqing Gongkai Shuomingshu, 101148422, 26 Mar. 2008 and Guangpu Shiyanshi, 23(1), 136-137.

Non limiting examples of solvents for the condensation step d) comprise pentane, cyclopentane, hexane, cyclohexane, benzene, toluene, 1,4-dioxane, chloroform, diethyl ether, dichloromethane, tetrahydrofuran, methyl-tetrahydrofuran, ethyl acetate, acetone, dimethylformamide, acetonitrile, dimethyl sulfoxide, n-butanol, isopropanol, n-propanol, ethanol, methanol and mixtures thereof, preferably ethanol.

The condensation step d) can be performed at temperature from −20° C. to 78° C., preferably 78° C.

V.d. The step e) consists of performing a reduction by reacting 2-methoxymethyl-[1,4]-benzoquinone dioxime (vi-a) in presence of a reducing agent and a reductive amination catalyst and one or more solvents to prepare 2-methoxymethyl-1,4-benzenediamine (iv-a):

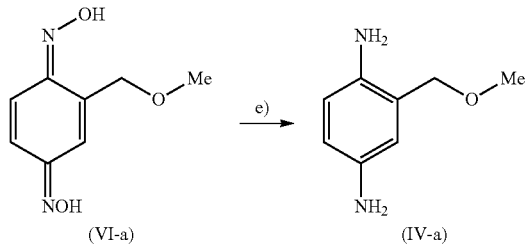

Finally the dioxime (VI-a) can be reduced to 2-methoxymethyl 1,4-benzenediamine (IV-a) with Raney Nickel and hydrazine according to a method adapted from Guangpu Shiyanshi, 23(1), 136-137; 2006. Additional methods that might be employed involving the use of hydrogen gas and Raney Ni catalyst are described in an improved process for the preparation of substituted aromatic diamines, Indian (1986), IN 158329 A1 19861018.

Non limiting examples of solvents for the reductive step e) comprise pentane, cyclopentane, hexane, cyclohexane, benzene, toluene, 1,4-dioxane, diethyl ether, tetrahydrofuran, methyl-tetrahydrofuran, dimethylformamide, acetonitrile, dimethyl sulfoxide, n-butanol, isopropanol, n-propanol, ethanol, methanol and mixtures thereof, preferably ethanol.

A reducing agent for the reductive step e) can be hydrazine.

The appropriate reductive amination catalyst can be Raney Nickel.

The reduction step e) can be performed at temperature from −20° C. to 100° C., preferably at 25° C.

VI. An additional step f) consists of transforming compound (iv) in presence of an acid mhz and one or more solvents into a salt of the formula (vii):

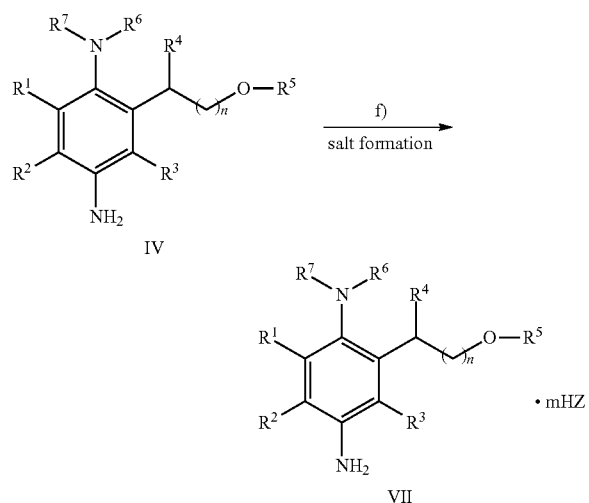

wherein $R^1$, $R^2$, $R^3$, $R^4$, $R^5$, $R^6$ and $R^7$ are substituents and n is an indicia as defined previously.

Non limiting examples of solvents for the salt formation step f) comprise pentane, cyclopentane, hexane, cyclohexane, benzene, toluene, 1,4-dioxane, chloroform, diethyl ether, dichloromethane, tetrahydrofuran, methyl-tetrahydrofuran, ethyl acetate, acetone, dimethylformamide, acetonitrile, dimethyl sulfoxide, n-butanol, isopropanol, n-propanol, ethanol, methanol and mixtures thereof, more preferably ethanol and water.

Non limiting examples of acid mHZ for the salt formation step f) can be selected from the group consisting of D,L-malic acid, L-malic, D-malic, hydrochloric, hydrobromic, citric, acetic, lactic, succinic, tartaric, or sulfuric acids and mixtures thereof.

By HZ is meant any acid having an acid proton "H". "Z" represents the rest of the molecule. For example if HZ=HCl, then Z=Cl. Another example can be if HZ=$CH_3CO_2H$, then Z=CH $CH_3CO_2$.

The value for "m" can be for 2, preferably m=1.

The skilled person would judge on the necessity to use a protecting when performing the process of this invention. If the skilled person decides to use a protecting group in the process described above, he will decide accordingly when to remove it. The use of protecting groups for the process of this invention is merely optional. Protecting groups are widely used in chemistry and the skilled person willing to use protecting groups during the process described in this invention would also judge on the appropriate step during the process to remove them in order to reach compounds of formula IV.

He will use his common general knowledge and books dedicated to that purpose such as "Greene's Protective Groups in Organic Synthesis" by Peter G. M. Wuts, Theodora W. Greene, Wiley-Interscience; 4 edition (Oct. 30, 2006) or "Protecting groups" by Philip J. Kocienski, Thieme, Stuttgart; Auflage: 3rd Revised edition (14. February 2005).

And consequently, if the skilled person decides to use a protecting group during the process, he would then decide to add extra deprotection step, to remove the protecting group. The deprotection conditions could also be found in the books cited above.

EXAMPLE

The present invention is further illustrated by the non limiting example that follows.

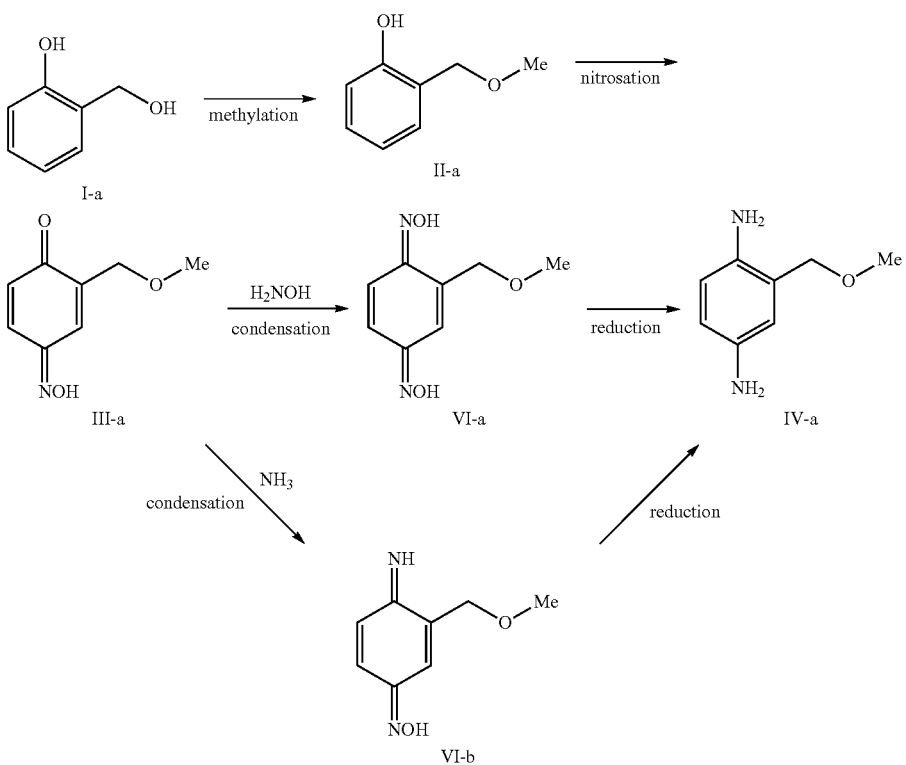

Experimental:
1. Synthesis of 2-methoxymethyl-phenol II-a

2-Hydroxybenzyl alcohol (10 g, 80.55 mmol) is dissolved in dry methanol (150 mL) and transferred to a Pyrex pressure bottle which is internally threaded and fitted with a double o-ring screw cap. The mixture is then heated (150° C.) for 1 h. Evaporation provides 10.8 g (98%) of a dark brown oil which is used directly in the next reaction; $^1$H-NMR (500 MHz, CDCl$_3$); δ 3.42 (s, 3 H), 4.69 (s, 2 H), 6.8-7.22 (m, 4 H), 7.78 (s, 1 H).

2. Synthesis of 2-methoxymethyl-4-nitrosophenol III-a

2-Methoxymethylphenol (1.0 g, 7.24 mmol) is suspended in water (10-25 mL) at room temperature, and then cooled down to 0° C. using an ice-water bath. With internal monitoring of pH, 6M H$_2$SO$_4$ is added until pH begins to decrease. The solutions of 6M H$_2$SO$_4$ and 6M NaNO$_2$ are added in an iterative manner to keep the pH at about 2.0. On this scale, the pH fluctuates from 1.5 to 2.5. Once the addition is complete, a brown solid starts to precipitate. Filtration provides 530 mg (53%) of 2-methoxyl-4-nitrosophenol III-a; $^1$H-NMR (500 MHz, CDCl$_3$) δ 3.49 (s, 3 H), 4.33-4.35 (d, 2 H), 6.51 (d, 1 H), 7.20-7.22 (d, 1 H), 7.76-7.78 (d, 1 H), 9.65 (s, 1 H).

3. Synthesis of 2-methoxymethyl-1,4-quinone dioxime VI-a

2-Methoxymethyl-4-nitrosophenol III-a (1.21 g, 2.99 mmol) is dissolved in anhydrous ethanol (10-20 mL). Hydroxylamine hydrochloride (2.52 g, 36.36 mmol) and potassium carbonate (1.6 mg, 11.57 mmol) are added and reflux initiated. After 4 h at reflux, 2.52 g of additional hydroxylamine hydrochloride is added. After evaporation of the solvent, the residue is then dissolved in a mixture of ethyl acetate (100 mL) and 1N HCl (25 mL) and washed two times with 1N HCl (2×25 mL). After evaporation of the excess of ethyl acetate, the product obtained (1.32 g) is sufficiently pure to be used for the next step; Yield=quant; $^1$H-NMR (500 MHz, CD$_3$OD) δ 3.33-3.45 (m, 3 H), 4.6 (s, 2 H), 6.6-6.68 (m, 1 H), 7.22-7.38 (m, 2 H).

4. Synthesis of 2-methoxymethyl-1,4-benzenediamine IV-a

2-Methoxymethyl-1,4-quinone dioxime (910 mg, 4.97 mmol) is dissolved in ethanol (2-5 mL). Raney Nickel (420 mg) is added into the mixture, followed by hydrazine (1.36 mL, 433 mmol). The mixture is stirred at room temperature for 1 h. The excess of ethanol is evaporated under vacuum. The residue is then dissolved in a mixture of dicholoromethane (125 mL) and water (50 mL), followed by addition of saturated NaCl (25 mL) to break up the emulsion. The resulting mixture is extracted with dichloromethane (3×75 mL). The organic phases are then combined and evaporated under vacuum to provide 630 mg of IV-a (83% yield); $^1$H-NMR (500 MHz, CDCl$_3$) δ 3.2-3.9 (m, 7 H), 4.39 (s, 2 H), 6.5 (s, 1 H), 6.56 (s, 2 H).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for the preparation 1,4-diamino-2-methoxymethylbenzene (IV-a), its derivatives of formula (IV), and the salts thereof comprising the steps of:
   (a) inserting a nitroso function to compounds of formula (II) in the presence of a nitrosation agent and one or more solvents to prepare compounds of formula (III)

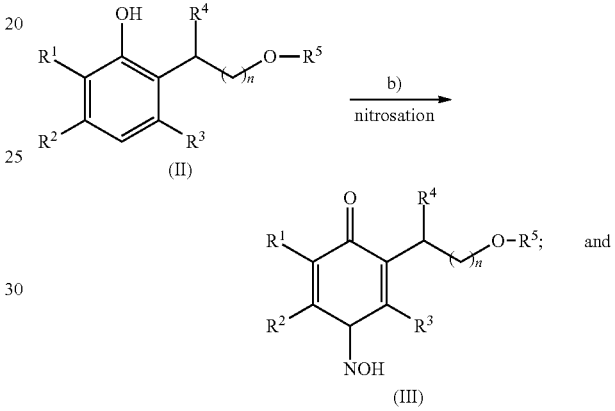

(b) performing a reductive amination of compounds of formula (III) in the presence of an amine reducing agent, a reductive amination catalyst and one or more solvents to prepare compounds of formula (IV):

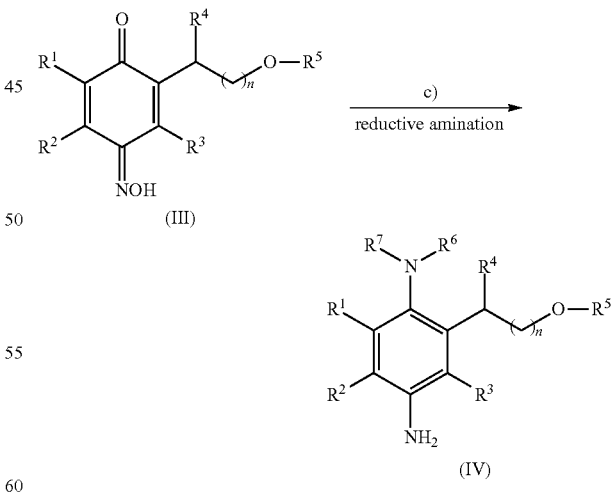

wherein $R^1$, $R^2$, $R^3$ are substituents independently selected from the group consisting of:
(a) C-linked substituents selected from the group consisting of:
   (i) mono- or poly-substituted or unsubstituted, straight or branched, aliphatic, heteroaliphatic, (ii) mono- or poly-substituted or unsubstituted, mono- or poly-unsaturated aryl systems, and (iii) mono- or poly-substituted or unsubstituted, mono- or poly-unsaturated heteroaryl systems, and wherein said systems of (i), (ii) and (iii) comprise from about 1 to 10 carbon atoms and from about 0 to 5 heteroatoms selected from the group consisting of O, F, N, P and Si;

(b) S-linked substituents selected from the group consisting of $SA^1$, $SO_2A^1$, $SO_3A^1$, $SSA^1$, $SOA^1$, $SO_2NA^1A^2$, $SNA^1A^2$, and $SONA^1A^2$;

(c) O-linked substituents selected from the group consisting of $OA^1$, $ONA^1A^2$;

(d) N-linked substituents selected from the group consisting of $NA^1A^2$; $(NA^1A^2A^3)^+$, $NA^1SA^2$, $NO_2$; $NA^1A^2$;

(e) substituents selected from the group consisting of $COOA^1$, $CONA^1$, $CONA^1COA^2$, $C(=NA^1)NA^1A^2$, CN, and X;

(f) fluoroalkyl substituents selected from the group consisting of mono-, poly-, and per-fluoro alkyl systems comprising from 1 to 12 carbon atoms and from 0 to 4 heteroatoms; and (g) H;

and mixtures thereof;

wherein $A^1$, $A^2$, and $A^3$ are substituents independently selected from the group consisting of H; substituted or unsubstituted, straight or branched, alkyl, mono- or poly-unsaturated alkyl, heteroalkyl, aliphatic, heteroaliphatic, or heteroolefinic systems; substituted or unsubstituted, mono- or poly-cyclic aliphatic, aryl, or heterocyclic systems; and substituted or unsubstituted, mono-, poly-, or per-fluoro alkyl systems, or $A^1$ and $A^2$ together with nitrogen atoms to which they are bound form a ring; wherein said systems comprise from 1 to 10 carbon atoms and from 0 to 5 heteroatoms selected from the group consisting of O, S, N, P, and Si; and wherein X is a halogen selected from the group consisting of F, Cl, Br, I, and mixtures thereof;

wherein $R^4$ is a substituent independently selected from the group consisting of a hydrogen, mono- or poly-substituted or unsubstituted, straight or branched, aliphatic, heteroaliphatic and mixtures thereof;

wherein $R^5$ is a substituent independently selected from the group consisting of a hydrogen, mono- or poly-substituted or unsubstituted, straight or branched, aliphatic, heteroaliphatic and mixtures thereof;

wherein $R^6$ and $R^7$ is selected from the group consisting of hydrogen, hydroxyl, alkyl, hereo alkyl, mono or poly-hydroxyalkyl, mono or poly-hydroxy hetero alkyl;

wherein n is equal to 0, 1, 2, or 3.

2. A process according to claim 1 further comprising the step of alkylating compounds of formula (I) in the presence of an alkylating agent and one or more solvents to prepare compounds of formula (II),

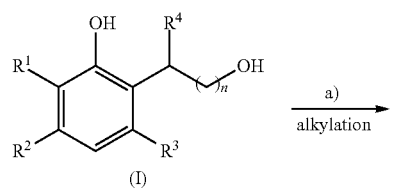

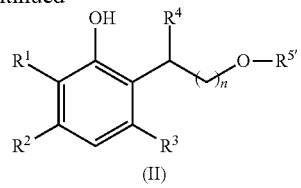

wherein $R^1$, $R^2$, $R^3$, $R^4$ are substituents and n is an indicia as defined in claim 1; and wherein $R^{5'}$ is a substituent independently selected from the group consisting of a mono- or poly-substituted or unsubstituted, straight or branched, aliphatic, heteroaliphatic and mixtures thereof.

3. A process according to claim 1 further comprising the step of transforming of compound (IV) into a salt of the formula (VII) in presence of an acid mHZ and one more solvents:

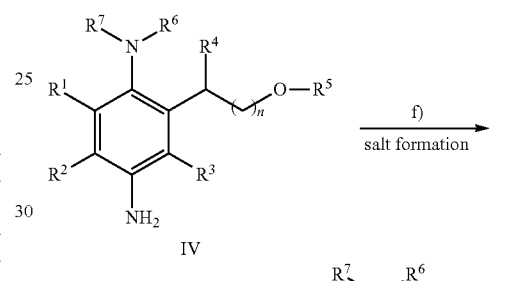

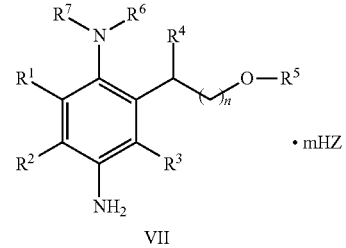

wherein $R^1$, $R^2$, $R^3$, $R^4$, $R^5$, $R^6$, $R^7$ are substituents and n is an indicia as defined in claim 1.

4. A process according to claim 3, wherein the acid HZ is selected from the group consisting of D,L-malic acid, L-malic, D-malic, hydrochloric, hydrobromic, citric, acetic, lactic, succinic, tartaric, or sulfuric acids and mixtures thereof and m=1 or 2.

5. A process according to claim 2, wherein the steps of b) nitrosation and c) reductive amination and a) alkylating, are performed successively in this order.

6. A process according to claim 2, wherein the steps of a) alkylating, b) nitrosation and c) reductive amination steps are performed successively in this order.

7. A process according to claim 2, wherein the alkylating agent is a nucleophilic alkylating agent or an electrophilic alkylating agent.

8. A process according according to claim 1, wherein the reductive amination step c) comprises the two successive steps of:

performing a condensation step d) by reacting compounds of formula (III) in presence of an amine $R^6R^7NH$ and one or more solvents to prepare compounds of formula (VI):

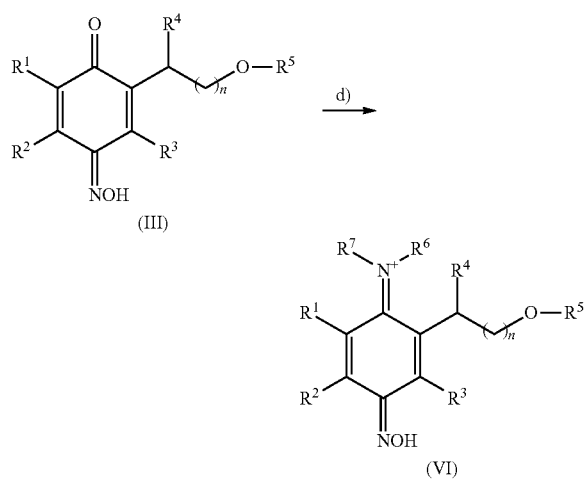

(III)

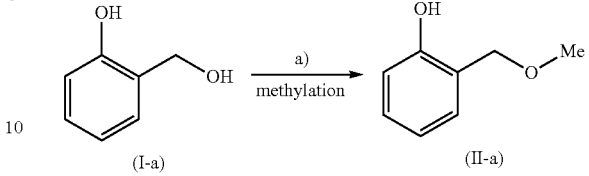

wherein $R^6$ and $R^7$ is selected from the group consisting of hydrogen, hydroxyl, alkyl, hereo alkyl, mono or poly-hydroxyalkyl, mono or poly-hydroxy hetero alkyl;
wherein $R^1$, $R^2$, $R^3$, $R^4$, $R^5$ are substituents and n is an indicia as defined in claim 1; and subsequently
performing a reductive step e) by reacting compounds of formula (VI) in presence of a reducing agent, and optionally a reductive amination catalyst and one or more solvents to prepare compounds of formula (IV):

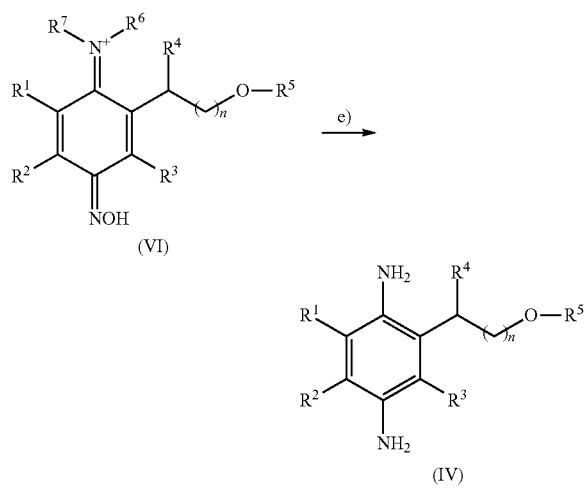

wherein $R^6$ and $R^7$ is selected from the group consisting of hydrogen, hydroxyl, alkyl, hereo alkyl, mono or poly-hydroxyalkyl, mono or poly-hydroxy hetero alkyl;
wherein $R^1$, $R^2$, $R^3$, $R^4$, $R^5$ are substituents and n is an indicia as defined in claim 1.

9. A process according to claim 8, wherein the reducing agent comprises hydrazine, $H_2$, $LiAlH_4$, $LiBH_4$, DiBAl, $NaBH_4$, $NaCNBH_3$, $B_2H_6$, sodium hydrosulfite, sodium sulfide, and mixtures of thereof.

10. A process according to claim 8, wherein the reductive amination catalyst is selected from the group consisting of Raney nickel, nickel, palladium, Lindlar catalyst, cobalt, copper chromite, platinum, platinum oxide, rhenium, tin(II) chloride, titanium(III) chloride, zinc, samarium, iron and mixtures thereof.

11. A process for making 2-methoxymethyl-benzene-1,4-diamine comprising the steps of:
a) methylating 2-hydroxymethyl-phenol (I-a) in methanol to prepare 2-methoxymethyl-phenol (II-a);

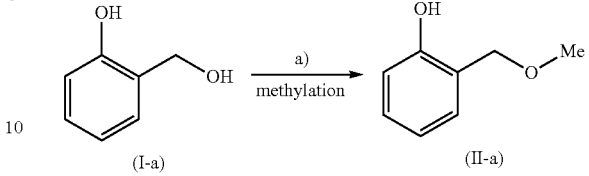

wherein Me represents a methyl group;
b) inserting a nitroso function to 2-methoxymethyl-phenol (II-a) in presence of a source of nitroso function and one or more solvents to prepare 2-methoxymethyl[1,4]-benzoquinone 4-oxime (III-a);

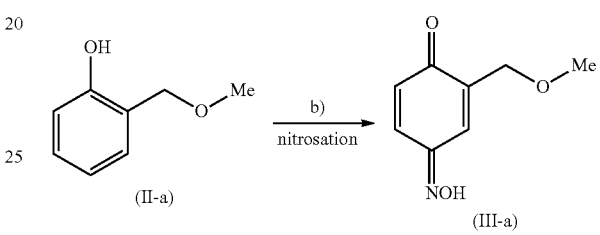

wherein Me represents a methyl group;
d) performing a condensation step by reacting 2-methoxymethyl[1,4]-benzoquinone 4-oxime (III-a) with hydroxylamine, in presence of a base and one or more solvents to prepare 2-methoxymethyl-[1,4]-benzoquinone dioxime (VI-a); and

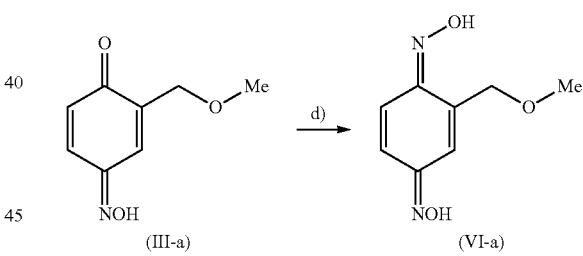

wherein Me represents a methyl group;
e) performing a reductive step by reacting 2-methoxymethyl[1,4]-benzoquinone dioxime (VI-a) in presence of a reducing agent and reductive amination catalyst and one or more solvents to prepare 2-methoxymethyl-benzene-1,4-diamine (IV-a);

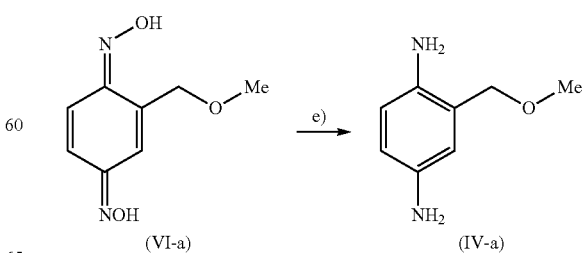

wherein Me represents a methyl group.

12. A process according to claim 11, wherein the methylation step a) is performed at a temperature from 0° C. to 200° C.

13. A process according to claim 11, wherein the source of nitroso function of the nitrosation step b) is $NaNO_2$ and $H_2SO_4$.

14. A process according to claim 11, wherein the nitrosation step b) is performed at acidic pH, wherein the pH range is from 1 to 4.

15. A process according to claim 11, wherein the solvent of the nitrosation step b) is selected from the group consisting of pentane, cyclopentane, hexane, cyclohexane, benzene, toluene, 1,4-dioxane, chloroform, diethyl ether, dichloromethane, tetrahydrofuran, methyl-tetrahydrofuran, ethyl acetate, acetone, dimethylformamide, acetonitrile, dimethyl sulfoxide, n-butanol, isopropanol, n-propanol, ethanol, methanol and mixtures thereof.

16. A process according to claim 11, wherein the nitrosation step b) is performed at 0° C.

17. A process according to claim 11, wherein in the reductive step e) the reducing agent is hydrazine, and the reductive amination catalyst is Raney Nickel.

18. A process according to claim 11, wherein the solvent of the reductive step e) is selected from the group consisting of pentane, cyclopentane, hexane, cyclohexane, benzene, toluene, 1,4-dioxane, chloroform, diethyl ether, dichloromethane, tetrahydrofuran, methyl-tetrahydrofuran, ethyl acetate, acetone, dimethylformamide, acetonitrile, dimethyl sulfoxide, n-butanol, isopropanol, n-propanol, ethanol, methanol and mixtures thereof.

19. A process according to claim 11, wherein the reduction step e) is performed at 25° C.

\* \* \* \* \*

UNITED STATES PATENT AND TRADEMARK OFFICE
CERTIFICATE OF CORRECTION

| | | |
|---|---|---|
| PATENT NO. | : 8,592,631 B2 | Page 1 of 1 |
| APPLICATION NO. | : 13/016272 | |
| DATED | : November 26, 2013 | |
| INVENTOR(S) | : John Michael Gardlik et al. | |

It is certified that error appears in the above-identified patent and that said Letters Patent is hereby corrected as shown below:

Title Page, Item (54) and in the Specification at Column 1, line 2, in the title, delete "2-methoxymethy1-1" and insert --2-methoxymethyl-1--.

Signed and Sealed this
Twenty-eighth Day of January, 2014

Michelle K. Lee
*Deputy Director of the United States Patent and Trademark Office*